United States Patent
Welch et al.

(10) Patent No.: US 10,646,347 B2
(45) Date of Patent: May 12, 2020

(54) PROTEIN DELIVERY WITH POROUS METALLIC STRUCTURE

(71) Applicant: Bioventus, LLC, Durham, NC (US)

(72) Inventors: Jeffrey Welch, Durham, NC (US); Eric Vanderploeg, Stoneham, MA (US); Christopher Wilson, Auburndale, MA (US); John Wozney, Hudson, MA (US)

(73) Assignee: Bioventus LLC., Durham, NC (US)

( * ) Notice: Subject to any disclaimer, the term of this patent is extended or adjusted under 35 U.S.C. 154(b) by 320 days.

(21) Appl. No.: 15/619,767

(22) Filed: Jun. 12, 2017

(65) Prior Publication Data
US 2017/0354504 A1    Dec. 14, 2017

Related U.S. Application Data

(60) Provisional application No. 62/348,163, filed on Jun. 10, 2016.

(51) Int. Cl.
| | |
|---|---|
| *A61F 2/30* | (2006.01) |
| *A61L 27/56* | (2006.01) |
| *A61L 27/06* | (2006.01) |
| *A61L 27/42* | (2006.01) |
| *A61L 27/22* | (2006.01) |
| *A61L 31/14* | (2006.01) |
| *A61F 2/28* | (2006.01) |
| *A61L 31/16* | (2006.01) |

(52) U.S. Cl.
CPC .......... *A61F 2/30767* (2013.01); *A61L 27/06* (2013.01); *A61L 27/227* (2013.01); *A61L 27/427* (2013.01); *A61L 27/56* (2013.01); *A61L 31/14* (2013.01); *A61F 2/28* (2013.01); *A61L 31/16* (2013.01); *A61L 2300/414* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,394,370 A | 7/1983 | Jefferies |
| 5,385,887 A | 1/1995 | Yim et al. |
| 7,722,895 B1 | 5/2010 | McKay et al. |
| 8,048,857 B2 | 11/2011 | McKay et al. |
| 8,153,148 B2 | 4/2012 | Maspero et al. |
| 8,952,131 B2 * | 2/2015 | Berasi .................... C07K 14/51 530/350 |
| 9,757,494 B2 | 9/2017 | Amedee et al. |

(Continued)

FOREIGN PATENT DOCUMENTS

| | | |
|---|---|---|
| CN | 104127913 A | 11/2014 |
| CN | 104353121 A | 2/2015 |

(Continued)

OTHER PUBLICATIONS

International Search Report and Written Opinion of PCT/US2017/036979, dated Aug. 18, 2017, 12 pages.

*Primary Examiner* — Carlos A Azpuru
*Assistant Examiner* — Casey S Hagopian (57) ABSTRACT

Osteoconductive synthetic bone grafts are provided in which porous metallic matrices are loaded with an osteoinductive protein. In certain embodiments, the grafts include porous ceramic granules deposited within the matrices.

35 Claims, 4 Drawing Sheets

(56) References Cited

U.S. PATENT DOCUMENTS

| | | | |
|---|---|---|---|
| 2002/0062154 A1* | 5/2002 | Ayers | A61F 2/28 |
| | | | 623/23.76 |
| 2003/0143258 A1* | 7/2003 | Knaack | A61F 2/28 |
| | | | 424/426 |
| 2005/0119761 A1 | 6/2005 | Matsumoto | |
| 2005/0209704 A1 | 9/2005 | Maspero et al. | |
| 2007/0178130 A1* | 8/2007 | McKay | A61L 24/0084 |
| | | | 424/423 |
| 2009/0169532 A1 | 7/2009 | Ying et al. | |
| 2009/0305983 A1 | 12/2009 | Ying et al. | |
| 2010/0248368 A1 | 9/2010 | Lynn et al. | |
| 2012/0219599 A1 | 8/2012 | Hans Moore et al. | |
| 2013/0224277 A1 | 8/2013 | Amedee et al. | |
| 2013/0287817 A1 | 10/2013 | Drapeau | |
| 2014/0308332 A1 | 10/2014 | Lynch et al. | |
| 2015/0328365 A1 | 11/2015 | Amedee et al. | |
| 2017/0319741 A1 | 11/2017 | Amedee et al. | |

FOREIGN PATENT DOCUMENTS

| | | |
|---|---|---|
| CN | 103357070 B | 5/2015 |
| EP | 1344538 | 9/2003 |
| JP | 2009528080 A | 8/2009 |
| JP | 2013540465 A | 11/2013 |
| JP | 2013545584 A | 12/2013 |
| WO | 9507108 A2 | 3/1995 |
| WO | 2002087475 A1 | 11/2002 |
| WO | 2005014072 A1 | 2/2005 |
| WO | 2006082442 A1 | 8/2006 |
| WO | 2013152418 A1 | 10/2013 |
| WO | 2016109555 A1 | 7/2016 |

* cited by examiner

PROTEIN DELIVERY WITH POROUS METALLIC STRUCTURE

RELATED APPLICATIONS

The present application claims priority to U.S. Provisional Application Ser. No. 62/348,163, filed on Jun. 10, 2016 and entitled "PROTEIN DELIVERY WITH POROUS METALLIC STRUCTURE".

FIELD OF THE INVENTION

This application relates to medical devices and biologic therapies, and more particularly to implants used for the repair and/or replacement of bone tissue.

BACKGROUND

Bone grafts are used in roughly two million orthopedic procedures each year, and general take one of three forms. Autografts, which typically consist of bone harvested from one site in a patient to be grafted to another site in the same patient, are the benchmark for bone grafting materials, inasmuch as these materials are simultaneously osteoconductive (serving as a scaffold for new bone growth), osteoinductive (promoting the development of osteoblasts) and osteogenic (containing osteoblasts which form new bone). However, limitations on the supply of autografts have necessitated the use of cadaver-derived allografts. These materials are less ideal than autografts, however, as allografts may trigger host-graft immune responses or may transmit infectious or prion diseases, and are often sterilized or treated to remove cells, eliminating their osteogenicity.

Given the shortcomings of human-derived bone graft materials, there has been a long-standing need in the field for synthetic bone graft materials. Synthetic grafts typically comprise calcium ceramics and/or cements delivered in the form of solid or granular implants, a paste or a putty. These materials are osteoconductive, but not osteoinductive or osteogenic. To improve their efficacy, synthetic calcium-containing materials have been loaded with osteoinductive materials, particularly bone morphogenetic proteins (BMPs), such as BMP-2, BMP-7, or other growth factors such as fibroblast growth factor (FGF), insulin-like growth factor (IGF), platelet-derived growth factor (PDGF), and/or transforming growth factor beta (TGF-β). However, significant technical challenges have prevented the efficient incorporation of osteoinductive materials into synthetic bone graft substitutes which, in turn, has limited the development of high-quality osteoinductive synthetic bone graft materials.

One such challenge has been the development of a graft matrix which delivers an osteoinductive material over time, rather than in a single short burst release, and which has appropriate physical characteristics to support new bone growth. The generation of a material with appropriate physical characteristics involves, among other things, balancing the requirement that such materials be rigid enough to bear loads that will be applied to the graft during and after implantation with the requirements that they remain porous enough to allow for cell and tissue infiltration and may degrade or dissolve at a rate which permits replacement of the graft by new bone, and the separate requirement that they elute the osteoinductive material in a temporal and spatial manner that is appropriate for bone generation. It is only the combination of the above design criteria that will result in an optimal graft matrix for promoting new bone formation and ultimate healing. For example, BMP-eluting synthetic bone grafts currently available commercially do not meet one or more of these requirements, and a need exists for a bone graft material which is optimized for the delivery of osteoinductive materials such as BMPs.

SUMMARY OF THE INVENTION

The present invention addresses an important unmet need in the field by providing synthetic bone graft materials with improved elution of osteoinductive proteins in combination with optimal physical characteristics, as well as methods of making and using the same. In one aspect, the present invention relates to compositions that include a porous biocompatible matrix with a plurality of micropores with an average size in the range of 50 to 500 microns, and an osteoinductive protein. In preferred embodiments, the osteoinductive protein is BMP-GER-NR or BMP-GER. In some embodiments, the osteoinductive protein is a BMP such as BMP-2, BMP-7, and the like or is a combination of BMP proteins, such as a combination of BMP-2 or BMP-7 with BMP-GER-NR or BMP-GER, for example. In some embodiments, the compositions include calcium ceramic granules (which optionally, but does not necessarily have a specific surface area greater than 30 $m^2/g$) contacting the biocompatible matrix, which granules have an interconnected network of micropores defining at least one surface on the interior of the granule. Compositions of the present invention can be configured for loading with an osteoinductive protein and to retain at least 50% of such osteoinductive protein for seven days or more after implantation into a patient.

In certain embodiments, the biocompatible implant comprises a porous metal matrix, such as stainless steel, titanium and titanium alloys, cobalt-chrome alloys, tantalum and the like. In a preferred embodiment, the invention provides a biocompatible implant comprising a matrix comprising nickel-titanium (NiTi or Ti—Ni) and more preferably, the Ti—Ni matrix has a porosity of 58%-68% and a plurality of micropores with a mean pore size between 50 and 500 microns; and an osteoinductive protein.

In certain embodiments, the porous matrix is characterized by one or more openings with an average diameter of at least 1-2 millimeters, in addition to a plurality of micropores having an average size in the range of from 50 to 500 microns. In other embodiments, the one or more openings have an average size of from 1 to 10 millimeters, preferably from 5 to 10 millimeters, or a single opening, preferably 10-20 millimeters in size. In another aspect, the present invention relates to a method of treating a patient that includes a step of contacting a bony tissue of the patient with the compositions of the present invention.

In yet another aspect, the present invention relates to a kit for treating a patient that includes a carrier and a vessel holding an osteoinductive protein in a form in which a fluid can be added to the osteoinductive protein to form a solution. The carrier includes a porous biocompatible matrix of the present invention and optionally, calcium ceramic granules in contact with the porous biocompatible matrix. The solution is formed by adding fluid to the vessel holding the osteoinductive protein, which is adapted to wet the carrier, and thereby associate the osteoinductive protein with at least one surface on the interior of the biocompatible matrix and granules that may be included in the composition, thereby forming an implant.

DESCRIPTION OF THE DRAWINGS

Certain embodiments of the present invention are illustrated by the accompanying figures. It will be understood

DETAILED DESCRIPTION

Osteoinductive Compositions

Synthetic bone grafts (also referred to interchangeably herein as "implants," "constructs" and "scaffolds") of the present invention generally include at least two components: an osteoinductive material such as a bone morphogenetic protein, and a biocompatible matrix comprising a porous metal. In certain embodiments, the grafts of the present invention also comprise an osteoconductive material such as a calcium ceramic in the form of granules or other solid mineral body. As used herein, osteoconductive materials refer to any material which facilitates the ingrowth or on growth of osteoblastic cells including osteoblasts, pre-osteoblasts, osteoprogenitor cells, mesenchymal stem cells and other cells which are capable of differentiating into or otherwise promoting the development of cells that synthesize and/or maintain skeletal tissue.

Osteoinductive materials generally include peptide and non-peptide growth factors that stimulate the generation of osteoblasts from populations of pre-cursor cells. In some embodiments, the osteoinductive material is a member of the transforming growth factor beta (TGF-β) superfamily such as BMP-2, BMP-3, BMP-4, BMP-5, BMP-6, BMP-7, BMP-9, or a designer BMP such as the BMP-GER or BMP-GER-NR chimeric BMPs described in U.S. Pat. No. 8,952,131 to Berasi et al. entitled "Designer Osteoinductive proteins," the entire disclosure of which is hereby incorporated by reference for all purposes. In certain embodiments, combinations of osteoinductive proteins may be used in the inventive implants, e.g., combination of BMP-2 and BMP-7 or BMP-GER-NR or BMP-GER and another BMP. In other embodiments, the osteoinductive material is a fibroblast growth factor, insulin-like growth factor, platelet-derived growth factor, a small molecule, a nucleotide, a lipid, or a combination of one or more of the factors listed herein. It is understood that the osteoinductive protein may be obtained from any source, e.g., human or a recombinant protein, for example.

Implants according to the present invention comprise a biocompatible matrix, which can be any suitable biocompatible material that exhibits sufficient rigidity and/or column strength to withstand the loads placed upon it when implanted, does not cause excessive inflammation (i.e., inflammation sufficient to inhibit or prevent the formation of new bone or the healing of a broken bone), inhibit the proliferation of osteoblasts, or otherwise interfere with the activity of the osteoinductive material, and has sufficient cohesion over an appropriate interval to permit the deposition of new bone within a defined area. In preferred embodiments, the biocompatible matrix includes a porous metallic material such as titanium-nickel (Ti—Ni) alloys. In an exemplary embodiment, the biocompatible matrix comprises a porous Ti—Ni intermetallic material such as that used in the Phusion Metal™ Cervical Cage (PorOsteon Inc., Menlo Park, Calif.) and described in U.S. Pat. No. 7,604,870, which is incorporated herein by reference for all purposes. Such materials preferably have an interconnected porosity of 53-73%, and more preferably 58-68%. In preferred embodiments, the Ti—Ni alloys used in the present invention have an atomic ratio of Ni:Ti varying from 0.96:1 to 1.13:1 and include a maximum concentration of 10 atomic percent of oxygen with the balance being Ni and Ti wherein the nickel concentration is limited to 53 atomic percent. In preferred embodiments, the Ti—Ni matrix has a porous structure in which less than 5 vol % of the pores are less than 50 microns in size, more than 75 vol % of the pores are 50-500 microns in size, and the balance of the pores are greater than 500 microns in size. In certain embodiments, the porous matrix is characterized by one or more openings with an average size of at least 1-2 millimeters in addition to the plurality of micropores. In some embodiments, the microporous matrix may comprise a "cage" having one or more openings, a.k.a. graft window(s), having an average size of from 5-10 mm or a single central opening of 10-20 mm.

In embodiments that include Ti—Ni intermetallic matrix materials, the matrix is preferably made using self-propagating high temperature synthesis reactions or other known processes such as sintering that yield a desired porous structure, as described in U.S. Pat. No. 7,604,870, incorporated herein in its entirety by reference thereto.

In preferred embodiments, the implants of the present invention include granules comprising an osteoconductive calcium phosphate ceramic that is adapted to provide sustained release of an osteoinductive substance that is loaded into or onto the granules. In some cases, the granules include interconnected, complex porous structures. When used, the osteoinductive substances (such as BMP) are loaded into the granules before the granules are loaded into the matrix. In other embodiments, the osteoinductive substances are loaded directly into the matrix without the use of granules. Exemplary granules, which the inventors have found exhibit BMP binding and elution characteristics that are optimized for use in constructs, systems and methods of the present invention, are described in U.S. patent application Ser. No. 14/983,008 to Vanderploeg et al., the entire disclosure of which is incorporated by reference herein for all purposes. These granules are associated (or "loaded") with osteoinductive materials such as BMPs using methods known in the art.

The granules are generally made of any suitable osteoconductive material having a composition and architecture appropriate to allow an implant of the invention to remain in place and to release osteoinductive material over time intervals optimal for the formation and healing of bone (e.g. weeks or months). While these characteristics may vary between applications, the granules generally include, without limitation, monocalcium phosphate monohydrate, dicalcium phosphate, dicalcium phosphate dehydrate, octocalcium phosphate, precipitated hydroxyapatite, precipitated amorphous calcium phosphate, monocalcium phosphate, alpha-tricalcium phosphate (α-TCP), beta-tricalcium phosphate (β-TCP), sintered hydroxyapatite, oxyapatite, tetracalcium phosphate, hydroxyapatite, calcium-deficient hydroxyapatite, and combinations thereof.

Implants of the invention generally have characteristics which are tailored to the facilitation of bone growth and healing and which are not exhibited by currently available synthetic bone grafting materials. The relevant characteristics of implants according to the present invention include at least (a) kinetics of release of osteoinductive materials that are appropriate for the application, (b) macroporosity that permits the infiltration of cells and tissues, including new vascular tissue that accompanies the formation of new bone, (c) microporosity of a matrix that facilitates incorporation of therapeutic amounts of osteoinductive protein onto the surfaces of the matrix and sufficient retention and release rates of the osteoinductive protein into surrounding tissue, and (d) sufficient rigidity/or and compression resistance to withstand loads applied to the implant.

Retention of Osteoinductive Molecules

Without wishing to be bound by any theory, it is thought that BMPs induce bone formation primarily by stimulating differentiation of osteoblast progenitors either resident at the site of repair in the bone envelope or in the surrounding soft tissue envelope. Physiological bone repairs are stimulated by the release of picogram/femtogram amounts of BMPs stored in the mineral phase of bone and from newly synthesized BMPs secreted by bone progenitor cells at the site of the repair. These two sources of BMP maintain BMP concentrations at the site of repair at physiological levels for the appropriate amount of time to induce a successful bone repair.

In view of this physiology, exogenous BMPs are, ideally, delivered in constructs which elute BMP in amounts and over intervals that mimic the physiological BMP response. Exogenous BMPs may be added to the implant constructs by applying a liquid solution of the BMP and allowing the BMP to adsorb onto and/or into the construct. Alternatively, BMPs may be incorporated into the manufacturing process of the implant construct such that they are entrapped within or associated with the construct prior to implantation. It should be noted, however, that the administration of much larger pharmacological BMP concentrations is generally required to achieve physiological concentrations of BMPs at the cellular level and to maintain the physiological concentrations for the appropriate amount of time. This is due to a combination of factors that are not totally understood. Without wishing to be bound by any theory, one factor driving the need for super-physiological BMP concentrations in these constructs may be the inability of exogenous BMP to mimic the efficiency of physiological local release of endogenous BMPs from bone and newly formed endogenous BMPs from cells. In addition, rhBMPs are generally insoluble at physiological pH, so (again, not wishing to be bound by any theory) much of the exogenously delivered BMP may not be physiologically available.

The amount of exogenous rhBMP required to stimulate bone repair appears to be species dependent. Empirical data suggest that lower concentrations of exogenous rhBMPs are required to stimulate bone formation in small animals such as rodents and rabbits compared to larger animals including dogs, sheep and goats. Nonhuman primates and humans appear to require the highest concentrations of exogenous rhBMPs to stimulate bone repair. For example, the FDA approved concentration of rhBMP-2 delivered in an absorbable collagen sponge (ACS) for bone repair in dogs is 0.2 mg/mL compared to 1.5 mg/mL in humans.

Similarly, the interval over which BMPs are optimally delivered to tissues varies among species: BMP residence time for repairs in rodents and rabbits can be as short as several days due to their rapid intrinsic rate of bone formation, while nonhuman primates and human patients generally require several weeks of BMP residence time. While not wishing to be bound by any theory, the longer interval observed in primates and humans appears to be related to the amount of time for the healing process to transition from an initial catabolic inflammatory phase caused by the surgery or trauma to an anabolic phase involving the migration and differentiation of osteoblast progenitors and associated new blood vessel units to support the fusion/repair process. Short BMP residence time optimal for rodents may not maintain physiological BMPs levels for a sufficient amount of time to stimulate bone repair in animals with slower bone formation rates. Conversely, BMP may not be released in sufficient amounts from a carrier with a longer retention profile to stimulate bone formation in animals with rapid intrinsic bone formation rates.

As one example, the residence time of BMPs delivered locally in buffer solution to a repair site is extremely short, and even when relatively large amounts of BMP are delivered in solution, an adequate bone response is only stimulated in rodent models. For applications in non-human primates and human patients, an extended-release carrier is preferably used to localize BMP to sites of treatment for a period of weeks.

One strategy for providing extended local BMP release is to utilize carriers that mimic the binding of BMP to endogenous extracellular matrix. As one example, ceramic carriers including calcium phosphate matrices (CPM) more closely mimic physiologic release of BMP from bone with very long residence times. The release of BMP from ceramic carriers may require the same osteoclastic resorption observed in release of BMP from bone. Based on this unique property, implants comprising ceramic components embedded within or associated with composite carriers, as are used in the present invention, may be superior vehicles for BMP delivery compared to other naturally occurring and synthetic biomaterials.

Example Constructs

The present invention encompasses a number of composite constructs that meet the design criteria discussed above. Table 1 sets forth several constructs according to various embodiments of the present invention, with "Design 1" including granules as discussed above, and "Design 2" being free from such granules. Furthermore, "Design 3" also includes a number of 1-2 mm diameter openings through the matrix. These designs provide embodiments suitable for loading of osteoinductive proteins, as described herein. This listing is exemplary rather than comprehensive, and it will be appreciated that other constructs which meet the design criteria above are within the scope of the present invention.

TABLE 1

EXEMPLARY CONSTRUCTS

| | Design 1 | Design 2 | Design 3 |
|---|---|---|---|
| Biocompatible Matrix | Ti-Ni intermetallic material— 50-500 μm pore size | Ti-Ni intermetallic material— 50-500 μm pore size | Ti-Ni intermetallic material— 50-500 μm pore size |

TABLE 1-continued

EXEMPLARY CONSTRUCTS

|  | Design 1 | Design 2 | Design 3 |
| --- | --- | --- | --- |
| Openings/ Fenestrations Through the Matrix | None | None | 1-2 mm diameter |
| Granule Size & Geometry | 225-800 μm, angular | None | None |
| Granule Density | 0.200-0.250 g/cc | N/A | N/A |
| Granule pH | 5.5-9.0 | N/A | N/A |

Example 1

Samples of Ti—Ni matrices representative of Phusion Metal™ Cervical Cage (PorOsteon Inc., Menlo Park, Calif.) were examined and loaded with BMP-GER-NR described in U.S. Pat. No. 8,952,131 and incorporated herein in its entirety.

Figure 1:
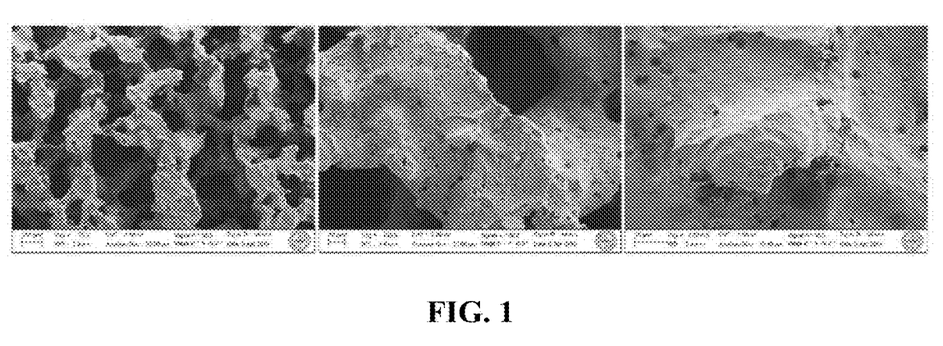
FIG. 1 shows scanning electron micrographs of porous metallic matrices used in the present invention, at 75×, 300× and 1500× magnification (from left to right).
Figure 2:
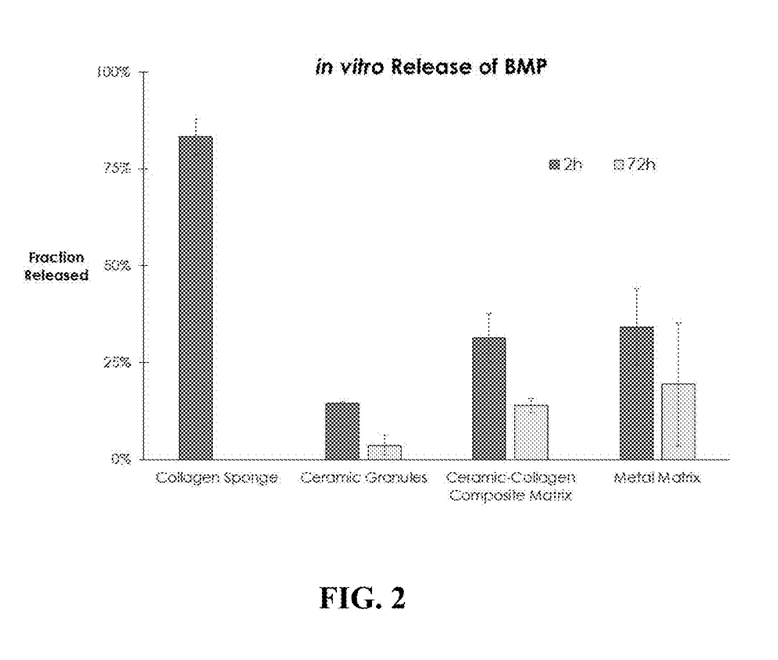
FIG. 2 shows the in vitro release of BMP-GER-NR by matrices of the present invention compared with collagen sponge, ceramic granules and ceramic-collagen composite matrix.

Scanning electron micrographs of the matrices are shown in FIG. 1, and demonstrate a highly rough and textured surface with features as small as 100 nm in size. BMP-GER-NR was loaded into the matrix by applying a protein solution (0.3 mg/mL in a pH 4 buffer solution) directly to the entire matrix in a volume equal to approximately 40-60% of the pore space within the matrix. The loaded matrices were allowed to stand for at least 15 minutes to enable the solution to fully penetrate the matrix, and then were placed into release buffer mimicking biological fluids comprised of saline and serum. Benchtop retention assays using ELISA were used to detect BMP-GER-NR in the release buffer at various time points. Approximately 34% of the initially loaded BMP-GER-NR was released after two hours, and another 19% was released after 72 hours. In comparison, similarly loaded absorbable collagen sponge (ACS) alone, calcium-deficient hydroxyapatite (CDHA) granules alone, and plant-based collagen matrices loaded with CDHA granules (as described in U.S. Ser. No. 62/333,571, which is incorporated herein by reference for all purposes) released 80%, 15% and 30% of BMP after two hours. These data are shown in FIG. 2 and demonstrate that the Ti—Ni porous matrix retained BMP with a release rate similar to that of CDHA granules, and collagen matrices loaded with CDHA granules.

Example 2

Figure 3:
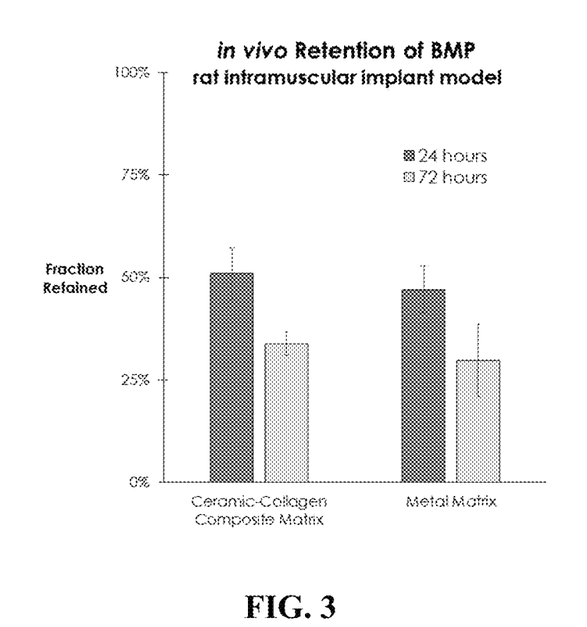
FIG. 3 shows the in vivo retention of BMP-GER-NR by porous metallic matrices used in the present invention compared to collagen in a rat intramuscular implant model.

An in vivo study in the rat intramuscular implant model was conducted to compare the retention of BMP-GER-NR by the Ti—Ni matrices with plant-based collagen matrices loaded with CDHA granules (as described in U.S. Ser. No. 62/333,571). Equal quantities of radiolabeled BMP-GER-NR solution were applied to samples of the Ti—Ni and collagen matrices for a time sufficient to allow absorption into the matrices, and then implanted into a quadriceps muscle pouch in rats. Quantitative scintigraphy was performed immediately after surgery, and then subsequently after 24 and 72 hours. BMP retention was similar at both 24 and 72 hours for the collagen sponges and Ti—Ni metal matrices, as shown in FIG. 3. These data indicate that the nature of the pore structure and surface characteristics of the Ti—Ni matrix are effective in retaining BMP-GER-NR on or near the matrix for a clinically-effective time period in vivo.

Example 3

Figure 4:
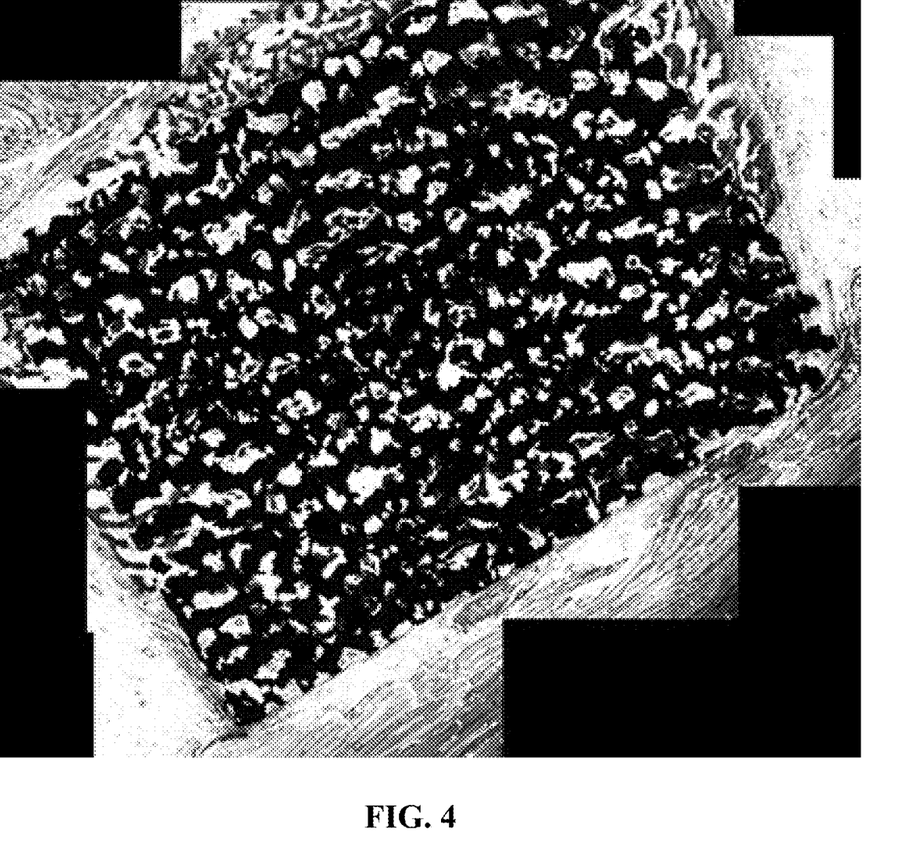
FIG. 4 shows a histological image of a matrix of the present invention that was contacted with a BMP containing solution and implanted into the quadriceps muscle of a rat for 14 day. New bone formation is evident surrounding and within the pore space of the implant matrix.
Figure 5:
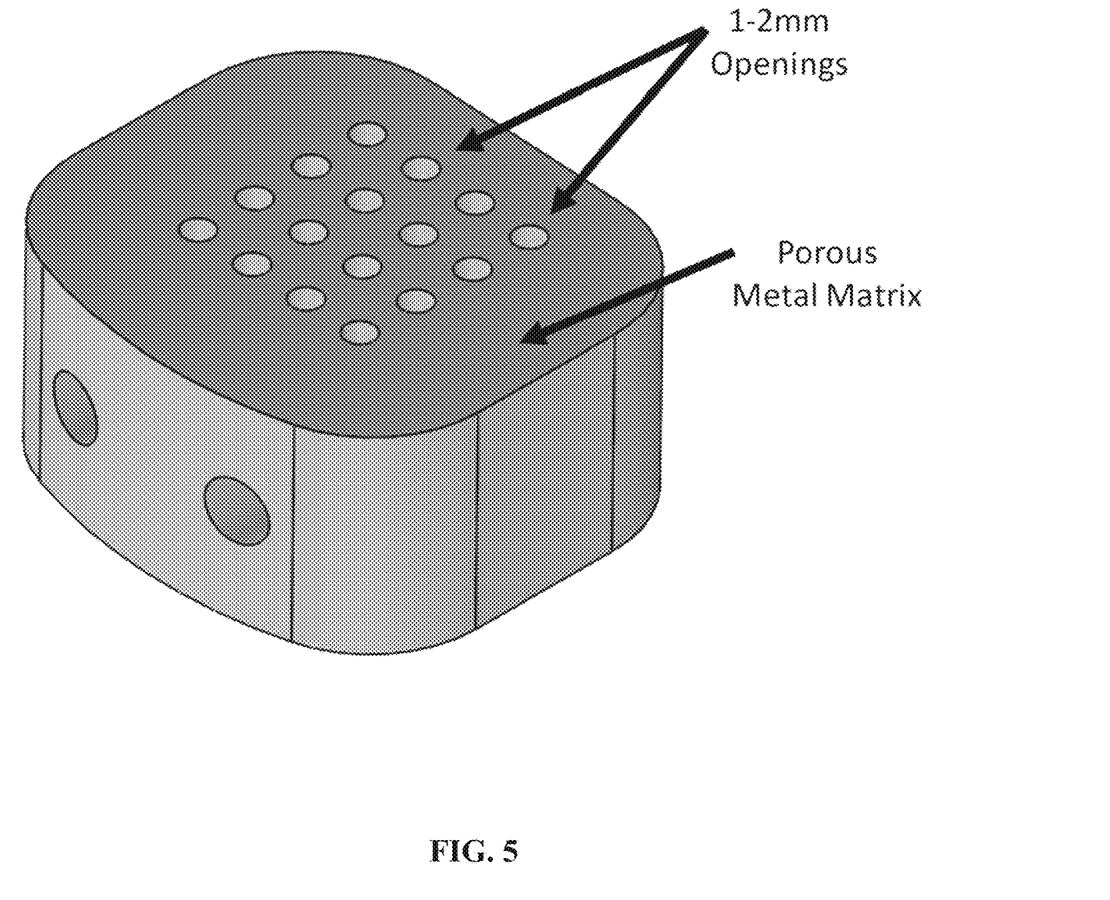
FIG. 5 is a schematic of an embodiment of the invention which shows a porous metallic matrix that has an array of 1-2 mm openings.

Separate Ti—Ni implants were loaded with either BMP-GER-NR or BMP-2 at a concentration of 0.1 mg/cc by applying a solution as described above directly to the matrix and then implanted into the intramuscular space in rats for 14 days. These samples were processed histologically to assess new bone formation. As shown in FIG. 4, new bone was found surrounding the implants and integrated into the porous space of the implants. These results were consistent across all implants tested. Additionally unlike many synthetic materials used in clinical bone repair applications, bone was found directly adjacent to the Ti—Ni implants without evidence of a fibrous layer encapsulating the implant. These findings suggest that the Ti—Ni matrices are capable of retaining BMP (here demonstrated with BMP-GER-NR and BMP-2) at the site of implantation for a clinically-effective length of time and that the matrices themselves can become integrated into the bone repair.

What is claimed is:

1. A biocompatible implant, comprising:
   a matrix comprising nitinol (Ti—Ni) comprising a plurality of pores, wherein the matrix has a porosity of 58%-68% and the plurality of pores have a mean pore size between 50 and 500 microns; and
   an osteoinductive protein;
   wherein the pores are randomly distributed throughout the matrix.

2. The biocompatible implant of claim 1, wherein said osteoinductive protein is bone morphogenic protein (BMP) BMP-GER-NR.

3. The biocompatible implant of claim 1, wherein said osteoinductive protein is bone morphogenic protein BMP-GER.

4. The biocompatible implant of claim 1, wherein said osteoinductive protein is bone morphogenic protein BMP-2.

5. The biocompatible implant of claim 1, wherein said osteoinductive protein is bone morphogenic protein BMP-7.

6. The implant of claim 1, wherein the atomic ratio of nickel to titanium in said matrix is between 0.96:1 and 1.13:1.

7. The implant of claim 1, wherein said matrix is characterized by one or more openings with an average diameter of at least 1-2 millimeters.

8. The implant of claim 1, wherein said matrix is characterized by one or more openings with an average size of from 5 to 10 millimeters.

9. The implant of claim 1, wherein said matrix is characterized by a single opening having an average size of from 10 to 20 millimeters.

10. A biocompatible implant, comprising:
    a matrix comprising Ti—Ni comprising a plurality of pores, wherein the matrix has a porosity of 58%-68% and the pores have a mean pore size between 50 and 500 microns; and
    an osteoinductive protein comprising BMP-GER-NR, and wherein the pores are randomly distributed throughout the matrix.

11. A biocompatible implant, comprising:
    a matrix comprising Ti—Ni comprising a plurality of pores, wherein the matrix has a porosity of 58%-68% and the pores have a mean pore size between 50 and 500 microns; and an osteoinductive protein comprising BMP-GER,
    wherein the pores are randomly distributed throughout the matrix.

12. A kit comprising the implant of claim 1.

13. The kit of claim 12, wherein the osteoinductive protein is lyophilized and provided in a container.

14. A kit comprising the implant of claim 10.

15. The kit of claim 14, wherein the osteoinductive protein is lyophilized and provided in a container.

16. A kit comprising the implant of claim 11.

17. The kit of claim 16 wherein the osteoinductive protein is lyophilized and provided in a container.

18. A method of treating a patient, comprising the steps of:
contacting a bony tissue of the patient with a biocompatible implant, said implant comprising:
a matrix comprising Ti—Ni having a plurality of pores, wherein the matrix has a porosity of 58%-68% and the pores have a mean pore size between 50 and 500 microns; and
an osteoinductive protein,
wherein the pores are randomly distributed throughout the matrix.

19. The biocompatible implant of claim 10, wherein the matrix further comprises one or more openings having an average size of from 1 to 2 millimeters.

20. The biocompatible implant of claim 11, wherein the matrix further comprises one or more openings having an average size of from 1 to 2 millimeters.

21. A biocompatible implant, comprising:
a matrix comprising Ti—Ni and a plurality of pores, wherein the matrix has a porosity of 58%-68% and the pores have a mean pore size between 50 and 500 microns;
an osteoinductive protein, and wherein the pores are randomly distributed throughout the matrix; and
a plurality of porous, calcium ceramic granules deposited within an open region of the matrix at a ratio of 150-310 milligrams of granules per cubic centimeter of matrix.

22. The implant of claim 21, wherein said osteoinductive protein is associated with said granules.

23. The implant of claim 21, wherein said osteoinductive protein is associated with said matrix.

24. The implant of claim 21, wherein the atomic ratio of nickel to titanium in said matrix is between 0.96:1 and 1.13:1.

25. The implant of claim 21, wherein said granules have an average size within the range of 225 to 800 microns.

26. The implant of claim 21, wherein said matrix is characterized by openings with an average size of 1-2 millimeters.

27. The implant of claim 21, wherein said calcium ceramic granules comprise calcium deficient hydroxyapatite.

28. The implant of claim 21, wherein said osteoinductive protein is BMP-GER-NR.

29. The implant of claim 21, wherein said osteoinductive protein is BMP-GER.

30. The implant of claim 21, wherein said osteoinductive protein is BMP-2.

31. The implant of claim 21, wherein said osteoinductive protein is BMP-7.

32. The biocompatible implant of claim 1, wherein the matrix has a porous structure in which less than 5 vol % of the pores are less than 50 microns in size, more than 75 vol % of the pores are 50-500 microns in size, and the balance of the pores are greater than 500 microns in size.

33. The biocompatible implant of claim 11, wherein the matrix has a porous structure in which less than 5 vol % of the pores are less than 50 microns in size, more than 75 vol % of the pores are 50-500 microns in size, and the balance of the pores are greater than 500 microns in size.

34. The method of claim 18, wherein the matrix has a porous structure in which less than 5 vol % of the pores are less than 50 microns in size, more than 75 vol % of the pores are 50-500 microns in size, and the balance of the pores are greater than 500 microns in size.

35. The biocompatible implant of claim 21, wherein the matrix has a porous structure in which less than 5 vol % of the pores are less than 50 microns in size, more than 75 vol % of the pores are 50-500 microns in size, and the balance of the pores are greater than 500 microns in size.

\* \* \* \* \*